(12) United States Patent
Paton (10) Patent No.: US 11,357,553 B2
(45) Date of Patent: Jun. 14, 2022

(54) ORTHOPAEDIC APPARATUS (71) Applicant: VetSOS Ltd, Shrewsbury (GB)

(72) Inventor: Rory M. Paton, Northwood (GB)

(73) Assignee: VetSOS Ltd., Shrewsbury (GB)

(*) Notice: Subject to any disclaimer, the term of this patent is extended or adjusted under 35 U.S.C. 154(b) by 0 days.

(21) Appl. No.: 16/463,778

(22) PCT Filed: Nov. 17, 2017

(86) PCT No.: PCT/EP2017/079694
§ 371 (c)(1),
(2) Date: May 23, 2019

(87) PCT Pub. No.: WO2018/095830
PCT Pub. Date: May 31, 2018

(65) Prior Publication Data
US 2019/0374266 A1    Dec. 12, 2019

(30) Foreign Application Priority Data
Nov. 24, 2016  (GB) ..................... 1619923

(51) Int. Cl.
*A61B 17/80* (2006.01)
*A61D 1/00* (2006.01)

(52) U.S. Cl.
CPC ...... *A61B 17/8014* (2013.01); *A61B 17/8057* (2013.01); *A61B 17/8061* (2013.01); *A61D 1/00* (2013.01)

(58) Field of Classification Search
CPC . A61B 17/80; A61B 17/8004; A61B 17/8014; A61B 17/8028; A61B 17/8052;
(Continued)

(56) References Cited

U.S. PATENT DOCUMENTS 5,269,784 A   12/1993  Mast
5,304,180 A    4/1994  Slocum
(Continued)

FOREIGN PATENT DOCUMENTS

CN    201260695 Y    6/2009
DE     20309361 U1   9/2003
(Continued)

OTHER PUBLICATIONS

International Search Report dated Feb. 19, 2018 for International Application No. PCT/EP2017/079694.
(Continued)

*Primary Examiner* — Zade Coley
*Assistant Examiner* — Diana Jones
(74) *Attorney, Agent, or Firm* — Cook Alex Ltd.

(57) ABSTRACT

A plate for securing two bone segments in a tibial plateau levelling osteotomy procedure having a body with an elongate distal portion and a proximal portion extending laterally and a plurality of apertures for receiving fixing means wherein at least two of the apertures are adapted to receive fixing means and at least one of the said apertures is adapted to receive a removable plug which extends proud of the bone-facing surface. One of the apertures has a camming surface configured such that upon insertion of the fixing means the bone fragments are urged together thereby promoting healing without deleterious compression of the surface of the bone.

17 Claims, 4 Drawing Sheets (58) Field of Classification Search
CPC .......... A61B 17/8057; A61B 17/8061; A61B 17/8095; A61D 1/00
See application file for complete search history.

(56) References Cited

U.S. PATENT DOCUMENTS

| | | | |
|---|---|---|---|
| 5,741,258 A | | 4/1998 | Klaue et al. |
| 6,540,746 B1 | | 4/2003 | Buhler et al. |
| 7,090,676 B2 | * | 8/2006 | Huebner ............ A61B 17/1728 606/71 |
| 7,282,053 B2 | * | 10/2007 | Orbay ................ A61B 17/8057 606/291 |
| 7,722,653 B2 | * | 5/2010 | Young ................ A61B 17/8052 606/280 |
| 8,808,333 B2 | * | 8/2014 | Kuster ................ A61B 17/74 606/280 |
| 2006/0149275 A1 | * | 7/2006 | Cadmus ............. A61B 17/8061 606/88 |
| 2007/0233106 A1 | * | 10/2007 | Horan ................ A61B 17/8061 606/282 |
| 2009/0234359 A1 | * | 9/2009 | Onoue ................ A61B 17/8009 606/71 |
| 2015/0127011 A1 | * | 5/2015 | Dunlop ................ A61B 17/842 606/88 |
| 2016/0128745 A1 | | 5/2016 | Sidebotham et al. |
| 2016/0166298 A1 | * | 6/2016 | Mighell ................ A61B 17/80 606/280 |

FOREIGN PATENT DOCUMENTS

| | | |
|---|---|---|
| EP | 2005978 A1 | 6/2008 |
| GB | 2532721 A | 6/2016 |
| WO | WO 2000/053110 A1 | 9/2000 |
| WO | WO 2004/075766 A1 | 9/2004 |
| WO | WO 2007/100513 A2 | 9/2007 |
| WO | WO 2011/163092 A2 | 12/2011 |
| WO | WO 2014/057405 A1 | 4/2014 |

OTHER PUBLICATIONS

UK Search Report dated Apr. 4, 2017 for GB Application No. GB1619923.4.

UK Search Report dated Jan. 14, 2019 for GB Application No. GB1719105.7.

UK Search Report dated May 2, 2018 for GB Application No. GB1719105.7.

DePuy Synthesis, LCP Locking Compression Plate—Surgical Technique, Jul. 7, 2016, See the 'Insert LCP spacers' section, p. 31, and the 'Spacers' section, p. 52.

DePuy Synthesis, TomoFix Medial Distal Femur (MDF)-For closed-wedge varus femoral osteotomies, Sep. 22, 2015, See the 'Preparing the implant' section, p. 5, and the 'Proximal fixation of the TomoFix femoral plate' section, p. 13.

* cited by examiner

ORTHOPAEDIC APPARATUS

CROSS-REFERENCE TO RELATED APPLICATIONS

This is a U.S. National Stage of International PCT Application No. PCT/EP2017/079694, filed Nov. 17, 2017 and claims the benefit of priority to Great Britain Application No. 1619923.4, filed Nov. 24, 2016, the disclosures of which are hereby incorporated by reference in their entireties.

BACKGROUND

This invention relates to an orthopaedic apparatus for use in a surgical procedure, particularly in a veterinary surgical procedure. In particular, the invention relates to an orthopaedic plate adapted for use with fixing means, especially screws, for use in fixing two bone segments in a fixed relationship for example a tibial plateau levelling osteotomy (TPLO) procedure and to a kit for use in a TPLO procedure. The invention also relates to a method of performing a TPLO procedure using the orthopaedic plate or kit.

The present invention is applicable to human surgery. And to veterinary surgery but is described with particular reference to veterinary surgery herein for convenience. A wide range of surgical procedures involving fixing segments of bones are well known in surgery, particularly in veterinary surgery. TPLO procedures are well known and commonly performed in veterinary surgery on animals having damaged or ruptured cranial cruciate ligaments (CrCL). The procedure is typically performed on canines particularly medium and large canines, and occasionally felines but may be performed on any animal requiring a TPLO procedure.

A TPLO procedure provides a means of stabilising the stifle/knee joint following damage to or rupture of the CrCL. The CrCL in its intact state retains the femur and tibia in a stable relationship but rupture or partial rupture of the CrCL causes instability between the femur and tibia, manifesting as the femur moving in an uncontrolled manner relative to the tibia, typically by sliding down the back of the upper portion of the tibia.

Figure 1:
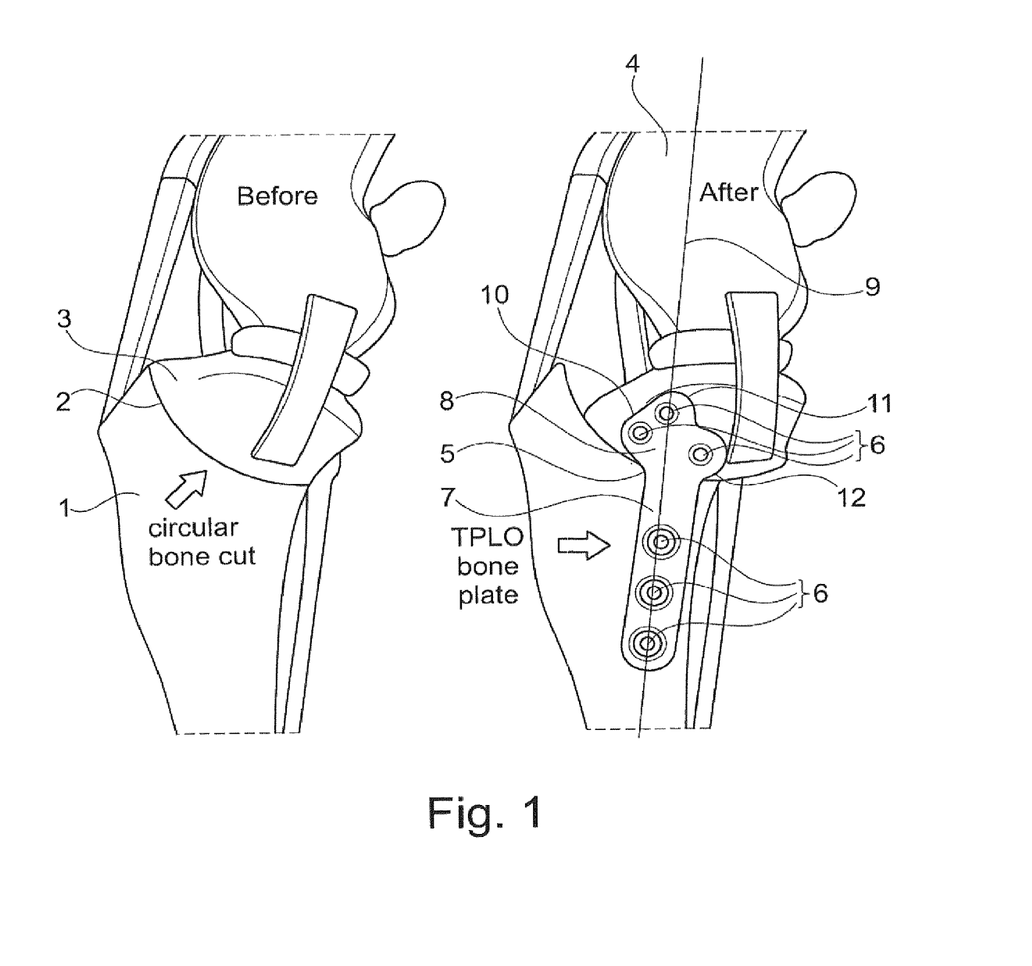
FIG. 1 shows a perspective view of a tibia and tibial fragment before and after a TPLO procedure with a conventional TPLO plate and is not according to the invention.

FIG. 1 shows a representation of a canine stifle/knee joint prior to a TPLO procedure being carried out and a representation after the procedure has been carried out with a conventional TPLO plate fixed in place. The TPLO procedure comprises cutting the upper part of the tibia 1 in a curvilinear locus, denoted by the line labelled 2, typically using a curved oscillating saw with a biradial blade, to provide a separated tibial fragment 3. The locus 2 has a fixed radius of curvature and the centre point through which radii taken from the locus pass is known as the intercondylar tibial eminence. The tibial fragment 3 is then moved by rotating it relative to the tibia 1 along the locus 2 to a position in which the upper surface of the tibial fragment 3 presents a more level surface upon which the femur 4 may rest and be secured in place using a TPLO plate 5 and associated screws 6. The tibial fragment is thereby held in its new location by the plate allowing the tibia and tibial fragment to heal whilst presenting a more level surface upon which the femur may locate.

Known TPLO plates may be fixed in place by a range of different types of screw or fixings for example 'AO' cortical screws, cortical self-tapping screws and locking screws.

In a TPLO procedure, surface compression of the bone, particularly the periosteum, by an orthopaedic plate as it is screwed to the bone may deleteriously interfere with the blood supply to the bone and lead to complication or infection which may necessitate further surgical intervention. Blood supply compromise has been well documented to slow healing and increase the chances of infection and subsequent need for further surgical intervention to remove the implants. Any subsequent surgical intervention is a revision procedure, which has associated increased risks of infection, exposes the patient to further risks of anaesthetic agents and incurs unacceptable and potentially avoidable additional financial and emotional burdens for patients and family members.

Locking screws and plates have been employed to minimise the risks associated with compression of the bone surface. Locking screws have a threaded shaft and head and are employed where the plate is to be held away from the surface of the bone to avoid surface compression. The plate will often but not always have threaded apertures and each locking screw will engage the bone and the plate aperture but in a manner that avoids pulling the plate onto the bone surface thereby avoiding compression of the bone surface. However, locking screws maintain the plate in a fixed relationship to the bone to which it is being affixed which does not allow the two bone fragments to be drawn together in a direction broadly parallel to the plane of the plate.

Bringing the two bone fragments together axially as a screw is inserted assists healing and minimises callus formation. Hitherto, in order to draw the bone fragments together, surgeons have had to employ "dynamic compression" or "limited contact dynamic compression plates" (LCDCP) plates which allow the bone fragments to be drawn together. Dynamic compression plates typically have an elongate aperture, commonly referred to as a "compression hole", which is aligned in a direction parallel with the intended direction of movement of the bone fragments. The aperture has a chamfered or slanted side and is typically ovoid in shape and the screw, for example a cortical screw, has a head complementary in shape to and which engages the side of the aperture and, in a camming effect, upon fixing urges the bone fragment to move axially relative to the plate such that the bone fragments approach and abut each other to facilitate healing.

However, known LCDCP/LDCP plates pull the plate towards the bone and risk disadvantageously compressing the bone. This drawback has been addressed to some extent by shaping the underside of the plate by scalloping out the plate between each hole to minimise the bone-plate contact area as the plate is pulled to the bone.

U.S. Pat. No. 5,304,180 describes a plate having a first subframe means 12 for overlying a tibial segment and which has two slots located therein and a second subframe means 14 in an elongate form for overlying a second tibial segment. The plate is adapted to receive conventional non-locking cortical screws. The screws pass through the plate and engage with the underlying bone and are independent of the plate. Whilst the bone segments may be brought together, the plate is susceptible to being compressed onto the surface of the bone segments.

US2006/0149275 describes a plate with a radial array of fixing points and employs eccentric guide holes which provide a means of generating a compressive force.

A need remains to provide a TPLO plate which reduces or avoids compression of the surface of the bone while allowing the bone fragments to be drawn together during fixing to promote healing.

SUMMARY

We have now devised a plate and method of carrying out a TPLO procedure in which one or more removable plugs are disposed in aperture(s) in the plate and which protrudes such that the plug extends proud of the bone-facing surface of the plate and act as a stilt for the plate upon placement on the bone. The combination of apertures enables the plate to be affixed to the bone and bone fragment in the appropriate location whilst held proud of the surface and the removable plug(s) removed and the plate further secured to the bone and bone fragment, Accordingly, in a first aspect, the invention provides a plate for securing two bone segments in a tibial plateau levelling osteotomy procedure comprising a body having a longitudinal axis, a bone-facing surface and an outer surface, opposed to the bone-facing surface, and further comprising an elongate distal portion and a proximal portion and a plurality of apertures wherein at least two of the apertures are adapted to receive fixing means and at least one of the said apertures is adapted to receive a removable plug which extends proud of the bone-facing surface.

In a second aspect, the invention provides a plate for securing two bone segments in a tibial plateau levelling osteotomy procedure comprising a body having a longitudinal axis, a bone-facing surface and an outer surface, opposed to the bone-facing surface, and further comprising an elongate distal portion and a proximal portion and a plurality of apertures wherein at least two of the apertures are adapted to receive fixing means and wherein at least one of the said apertures has a removable plug disposed in the aperture which extends proud of the bone-facing surface.

In a further aspect, the invention provides a plate for securing two bone segments in a tibial plateau levelling osteotomy procedure comprising a body having a longitudinal axis, and a plurality of apertures wherein at least two of the apertures are adapted to receive fixing means and wherein at least one of the said apertures comprises a camming surface and is configured to enable the transmission of a force applied to the fixing means in a direction parallel to the plane of the plate surrounding the aperture upon insertion of the fixing means.

Suitably, the plate comprises at least two apertures comprising a camming surface which allow the plate to be moved within the plane of the plate around the aperture upon insertion of fixing means, for example a compression screw into that aperture. Suitably, the at least two apertures are elongate with one aperture being aligned radially the intercondylar tibial eminence and the second elongate aperture being aligned orthogonally to the first elongate aperture. Preferably the second elongate aperture is located further than the first elongate aperture from the proximal portion of the plate.

Advantageously, the plate enables the tibia and the tibial fragment to be accurately aligned for direct bone healing to minimise callus formation whilst reducing the level and desirably substantially avoiding compression contact of the plate on the bone. This concept may be referred to as "offset compression" and advantageously allows the fixing means to be affixed to the bone with a lower force than conventionally required.

Preferably the plate is a polyaxial locking plate rather than a fixed angle locking plate.

The proximal portion of the body and the distal portion of the body are configured such that, when affixed in place, the distal portion generally overlies the tibia and the proximal portion generally overlies the tibial fragment such that the curvilinear locus of the cut 2 is overlain by the body between the proximal and distal portions. The bone-facing side of the body is suitably contoured such that the body snugly overlies the tibia and tibial fragment in an alignment in which the longitudinal axis of the plate is parallel or preferably coincident with the longitudinal axis of the tibia.

Suitably, the plurality of fixing apertures comprises a first plurality of fixing apertures adapted to receive fixing means in the distal portion and a second plurality of apertures in the proximal portion. Preferably the plate according to the invention has at least four apertures and desirably from five to ten apertures. At least one and suitably, at least two and optimally three of the said apertures has a removable plug disposed in the aperture that extends proud of the bone-facing surface. In a particularly preferred embodiment, the plate according to the invention is manufactured with removable plugs disposed in at least three apertures. More preferably, two apertures in the proximal portion have removable plugs located therein and one aperture in the distal portion has a plug located therein. The plugs are suitably located such that they protrude not more than 5 mm, preferably from 1 to 3 mm for example 2 mm from the plate, towards the bone. The plugs suitably allow the plate to be positioned such that it does not rock on the bone.

The plugs are removable from the aperture and suitably comprise means to retain the plug in a fixed position relative to the plate when inserted and during attachment of the plate to the tibial fragments until the surgeon removes the plugs. The plugs are suitably adapted to engage with the aperture in a manner which holds the plug in a fixed position relative to the plate while fixing means are inserted to secure the plate to the bone.

The removable plugs may comprise a screw thread adapted to engage with a complementary thread in the aperture in which the plug is removably inserted. The precise extent to which the plug protrudes may be selected by the surgeon in carrying out the osteotomy procedure.

As the plugs protrude, there is no requirement to scallop or otherwise shape the plate so that it sits evenly on the bone. Scalloping or shaping may however be employed if desired but is not necessary and preferably, the plate is not scalloped. By avoiding the need to shape the plate, the costs of production of the plate may be reduced. Beneficially, the underside contour of the plate may be kept to a simple anatomically congruent profile.

During the TPLO procedure, the plate is suitably located in the desired position by the surgeon, optionally using locating means, for example locating pins, sutures, forceps or the like. The plate rests on the tibia and tibial fragment via the removable plugs above the bone-facing surface such that the plate is not in contact with the bone to any substantial degree and desirably not at all. During the procedure, screws are suitably affixed with the plugs being removed, preferably sequentially, with the plugs in the apertures in the proximal portion being removed before the plug(s) in the distal portion.

The first plurality of apertures is suitably disposed in a generally longitudinal arrangement, parallel or coincident with the longitudinal axis of the plate. Preferably, the first plurality of apertures comprises one slot, one plate positioning aperture and at least two other apertures. The other apertures are adapted to receive fixing means and preferably are conventional screw holes and suitably are shaped to ensure the fixing means engage in a fixed relationship and are not movable in the plane of the distal portion. In a preferred embodiment, the first plurality of apertures comprises a slot, two screw holes and one plate positioning hole.

The slot is suitably a sole compression hole for use in a dynamic compression TPLO procedure.

The slot in the first plurality of apertures suitably is adapted to receive the head of a fixing means and dimensioned such that the head may move along and relative to the slot during fixing to the tibia underlying the distal portion. The slot is preferably located closer to the proximal portion than the other aperture(s) of the distal portion. The slot is suitably aligned in a direction facing the lateral lobe of the proximal portion and especially is aligned such that when position in use, the longitudinal axis of the slot intersects the curvilinear locus and is generally perpendicular to a tangent on the curvilinear locus at the intersection such that the axis of the slot passes through the intercondylar tibial eminence.

Advantageously, the perpendicular alignment allows the tibia and tibial fragment to move relatively in a direction perpendicular to the curvilinear cut upon securing the fixing means in the slot thereby increasing the likelihood of a close or snug positioning of the tibia and the tibial fragment to increase the chances of successful healing and reduced risk of infection.

Preferably, two apertures are slots, orthogonal to each other and disposed in the distal portion. Suitably at least one slot is aligned on a radius towards the intercondylar tibial eminence. Preferably a second slot is aligned cranially to provide a means of adjusting any cranial gap that may arise during rotation of the bone fragment.

The term "lateral" as employed herein refers to the spatial or geometric relationship of the features to which reference is made and does not imply any anatomical location for example lateral as opposed to medial, or relationship. When the plate is located on the tibia and tibial fragment, the lateral lobe of the proximal portion extends caudally, that is towards the rear of the subject.

The second plurality of apertures is suitably disposed towards the periphery of the proximal portion. Preferably, the second plurality of apertures comprises at least three apertures aligned in a triangular arrangement suitably with two apertures located laterally of the longitudinal axis of the body and a further aperture, generally on or near the longitudinal axis, preferably in alignment with apertures of the first plurality.

In one embodiment, the second plurality of apertures comprises three apertures for receiving fixing means with one aperture preferably located at or near the periphery of the lobe and the two further apertures located near the region in the proximal portion which is adjacent to the distal portion.

In a preferred embodiment the two apertures in a straight line are located such that upon fixing the plate to the tibia, the two apertures are located on or near a chord of the curvilinear cut between the tibia and the tibial fragment. In an especially preferred embodiment, the two apertures in the proximal portion define a line which is generally perpendicular to the axis of the slot in the distal portion. Upon securing the plate to the tibia using fixing means in the slot, the tibia and tibial fragment are drawn together and the location of the two aligned apertures in the proximal portion suitably enables a broadly evenly applied force to draw the tibia and tibial fragment together.

Preferably, the second plurality of apertures comprises conventional screw holes for fixing the plate to the tibial fragment and at least one positioning hole for locating the plate prior to fixing.

Preferably, the apertures in the body comprise a slot, positioning apertures and apertures for receiving fixing means. In a preferred embodiment, the apertures in the body comprise one positioning aperture S1 in the proximal portion, one positioning aperture S2 in the distal portion, two plug apertures F1 and F2 in the proximal portion, one plug aperture F4 in the distal portion and apertures F1, F2 and F3 in the proximal portion which are adapted to receive fixing means and at least two fixing apertures F4 and F5 in the distal portion and a fixing slot C1 in the distal portion. Preferably there are from six to eight fixing apertures. Preferably the positioning apertures are smaller than the fixing apertures and allow temporary stabilising pins for example arthrodesis wires and K-wires to be employed to facilitate placement and temporary plate apposition to the bone.

One or more plug aperture may also serve as a fixing aperture or the plug apertures may be different to the fixing apertures.

The slot C1 suitably has a chamfered or sloped profile. The fixing means suitably comprises a face for camming contact with the chamfered or sloped profile of the slot C1. The aperture or slot C1 may be oval or any other shape to allow the fixing means to move along the slot during fixing towards the fracture. Upon insertion, the fixing means engages with the underlying bone and also with the chamfered or sloped slot which acts as a camming surface to urge the fixing means towards the fracture, and thereby moves the underlying tibia 1 in which the fixing means is engaged relative to the plate thus effecting relative movement between the plate and the tibia 1. Insertion of the fixing means such as an AO cortical or cortical self-tapping screw accordingly brings the tibia and tibial fragment together.

Known DCP or LCDCP plates may be secured using cortical screws as discussed above but with the disadvantage of the underlying bone being crushed or damaged and impairing healing. Self-locking screws have also been employed which has a threaded head which engages with a thread on the inside of the aperture and thereby allow the plate to be fixed to the bone but without undue compression but also without the advantage of drawing the bone and bone fragment together.

The present invention allows the surgeon both to bring the tibia and tibial fragment together using the plate of the invention without causing undesirable or deleterious compression of the underlying bone's periosteal blood supply or periosteum.

Suitably, the fixing apertures are all compatible with for example existing standard 'AO' cortical, cortical self tapping and locking screws and any other locking screw system whether proprietary or generically available. Preferably the fixing apertures are suitable for use with polyaxial locking screws, for example the EVOLOX™ locking system available from N2-UK. The slot or compression hole is suitably compatible with AO cortical and cortical self-tapping screws. Advantageously, the plate according to the invention may be used with existing equipment such as surgical instrumentation and stock inventory such that practitioners do not need a new set of such equipment.

The apertures in the first plurality and second plurality for receiving fixing means to secure the plate in place suitably are disposed in locations over the optimal channels for each fixing means such that the longitudinal of the plate aligns directly with the proximal axis of the tibia. Known plates are typically configured such that upon fixing, they are angled in a caudoproximal to craniodistal alignment. Advantageously, alignment in the proximal axis of the tibia facilitates user-application and positioning of the plate.

In a preferred embodiment, the apertures for the removable plugs are suitably threaded and the plugs have threaded parts for engagement with the apertures. The inter-engagement between the plugs and the aperture allows the surgeon to select precisely the degree to which the plugs protrude from the plate so as to provide an optimal fit for the tibia upon which the procedure is being performed.

A range of plates of different shapes are known and are typically produced in a variety of sizes for use in procedures with animals of different sizes, for example from a Chihuahua to a Great Dane, with "left-hand" and "right-hand" plates being produced. Conventionally, a TPLO plate as shown in FIG. 1 comprises a distal portion 7 and a proximal portion 8 with the distal portion being an elongate shaft having a longitudinal axis 9 and the proximal portion comprising several lobes 10, 11 and 12 with at least one lobe 10, 12 on each side of the plate extending laterally of the longitudinal axis 9 to a greater degree than the distal portion 7 as shown in FIG. 1. The shape of the proximal portion is dictated by the required location of the screw apertures but the shape having multiple lobes is costly to produce.

TPLO plates are typically produced in six different sizes and, with left and right hand versions of each, the manufacturing process will typically be required to produce twelve plates having fixed relative dimensions. The need to be able to produce twelve different plates in a given shape or configuration requires flexibility in the manufacturing process whilst ensuring costs of manufacture are not prohibitively high, especially given that TPLO plates are used in large volumes. A need remains to reduce the costs of production of orthopaedic plates, particularly those for use in TPLO procedures.

In a further aspect, the invention provides a plate for securing two bone segments in a tibial plateau levelling osteotomy procedure comprising a body having a longitudinal axis, wherein the body comprises an elongate distal portion and a proximal portion and is shaped such that a first edge of the distal portion and a first edge of the proximal portion together form a linear edge which extends along the length of the body and is generally parallel to the longitudinal axis wherein the body comprises a first plurality of fixing apertures adapted to receive fixing means in the distal portion and a second plurality of apertures in the proximal portion.

Preferably the shape of the body of the plate maps onto the typical resulting shape of the tibia and tibial fragment after the TPLO procedure has been performed. Suitably the first plurality and second plurality of apertures are of a type and located in the positions as described above in relation to the first aspect of the invention.

The distal portion suitably has a second edge which is generally parallel to the first edge of the distal portion such that the distal portion is of elongate shape.

The proximal portion suitably has a second edge which defines a lobe which lobe extends laterally of the longitudinal axis. When the plate is located in use, the lobe extends caudally. The lateral lobe of the proximal portion suitably is dimensioned and located to overlie a part of the tibial fragment that extends beyond or "overhangs" the line of the uncut tibia.

The plate according to the invention may comprise measurement markings, for example a rule. Any such markings may be located along the top edge of the plate or along the straight edge along the distal and proximal portions. The presence of measurement marks aids usage and avoids the surgeon needing to acquire a separate measurement device.

The invention further provides an orthopaedic apparatus kit comprising a plate according to the invention in combination with fixing means.

The kit may comprise a plurality of plates of different sizes for ease of matching with the particular anatomy. Suitably the kit comprises left-hand and right-hand plates, being mirror images, to enable procedures on the left leg and right leg of a subject to be performed.

The invention is described by reference to the following non-limiting examples.

DESCRIPTION OF THE ILLUSTRATED EMBODIMENTS

As described above, FIG. 1 shows a representation of a canine stifle/knee joint prior to a TPLO procedure being carried out and a representation after the procedure has been carried out with a conventional TPLO plate fixed in place showing the upper part of the tibia 1, a curvilinear locus to be cut 2, a separated tibial fragment 3 which is moved by rotating relative to the tibia 1 along the locus 2 to a position in which the upper surface of the tibial fragment 3 presents a more level surface upon which the femur 4 may rest and secured in place using a TPLO plate 5 and associated screws 6. The curvilinear locus is centred on the intercondylar tibial eminence which, typically in most subjects, is just to the cranial direction of the point at which the medial collateral ligament traverses the stifle.

The body 5 comprises a distal portion 7 and a proximal portion 8 with the distal portion being an elongate shaft having a longitudinal axis 9. Lobes 10, 11 and 12 are provided with at least one lobe 10, 12 located on each side of the body 5 and extending laterally of the longitudinal axis 9.

Figure 2:
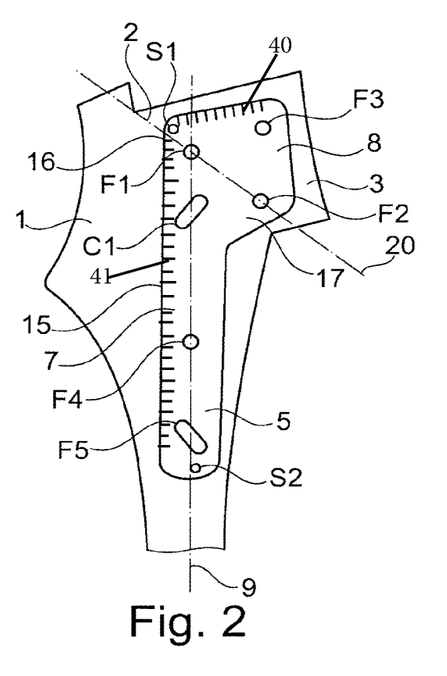
FIG. 2 shows a plan view of a plate according to the invention.
Figure 3:
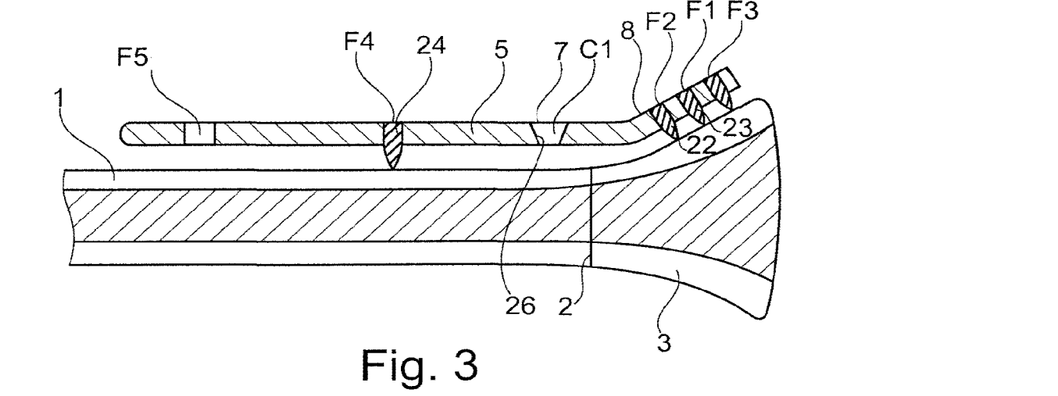
FIG. 3 shows a side elevation of a plate according to the invention with removable plugs in place.

FIG. 2 shows a plate according to the invention having a body 5 with distal and proximal portions 7, 8 which respectively are located and overlie the tibia 1 and tibial fragment 3 either side of the locus of the cut 2. The distal portion 7 and the proximal portion 8 lie in different planes as shown in FIG. 3. A first edge 15 of the distal portion 7 and a first edge 16 of the proximal portion 8 present a continuous edge to the body 5.

The proximal portion and the distal portion suitably lie in different planes so as to conform to the contours of the tibia and tibial fragment.

The proximal portion 8 has a lobe 17 which extends laterally of the longitudinal axis 9 to a greater extent than that part of the distal portion 7 lying on the same side of the body 5 so the lobe 17 may accommodate several apertures. The outline of the body as shown in the plan views of FIG. 2 generally maps the shape of the tibia 1 and tibial fragment 3 when fixed according to the TPLO procedure.

Figure 6:
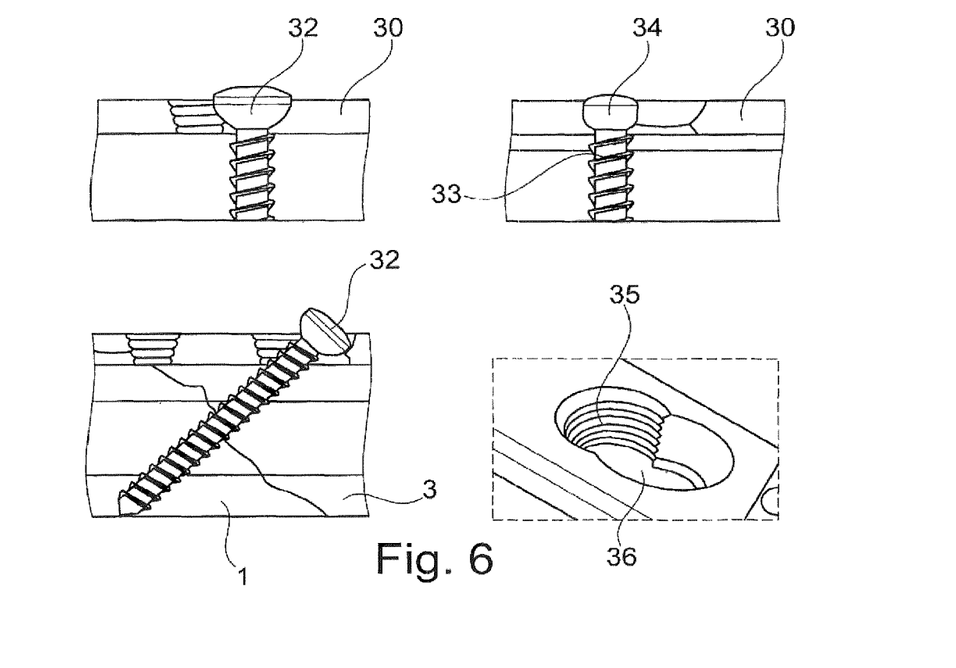
FIG. 6 shows known fixing means and a threaded aperture suitable for use with the invention.
Figure 7:
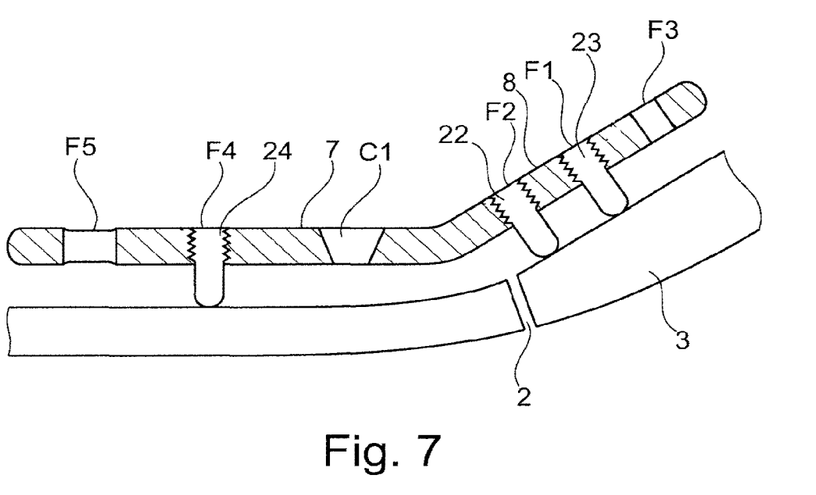
FIG. 7 shows a cross-sectional side elevation of a plate as shown in FIG. 3 with threaded apertures.

FIG. 2 shows a plate with six fixing apertures suitable for use with a standard size canine. The tibia 1 and tibial fragment 3 have been cut by a biradial saw to produce a locus 2 which is centred about intercondylar tibial eminence X. Radii r and r' of generally equal length, due to the constant radius of curvature of the cut are shown. The plate has fixing apertures F1, F2 and F3 located in the proximal portion 8 with apertures F1 and F2 being located generally on a chord 20 of the locus 2 and aperture F3 located in the lobe 17 more distant from the locus 2 than from the chord 20. Aperture F1 is suitably located at or near to the longitudinal axis 9. Positioning aperture S1 allows the plate to be temporarily fixed in place during the surgical procedure. Apertures F1 and F2 have a removable plug which is removed during the plate fixing procedure and replaced by screws for example locking screws as shown in FIG. 6. A plate with the removable plugs 22, 23, 24 in place is shown in cross-section in FIG. 3. The removable plug suitably is located in the aperture such that the degree to which the plug protrudes may be closely controlled to tailor the positioning of the plate, particularly the distance of the plate above the bone, to the particular topography of the bone. By way of example, the removable plug may have a screw thread which engages with a complementary thread on the inner wall of the aperture as shown in FIG. 7. Alternatively, the plug may be dimensioned so as to provide a push-fit within the aperture and be readily removable during the TPLO procedure as appropriate. The precise extent to which the plug protrudes proud of the plate may then be adjusted during the TPLO procedure.

Distal portion 7 has fixing apertures F4 and C2/F5 and compression slot C1 arranged in a generally linear manner and coincident with longitudinal axis 9. Aperture C2/F5 may be a fixing aperture F5 or a compression slot C2 in which case it is suitably is aligned cranially and, more preferably, is broadly perpendicular to the radius of a circle centred on slot C1. Insertion of a compression fixing means into compression slot C2 after insertion of fixing means in fixing aperture F3 enables bone fragment 3 to be rotated anticlockwise (cranially) as viewed in FIG. 2 or 4. In practice, a small gap may arise between the upper part of fragment 3 and tibia 1 as the surgeon rotates fragment 3 and compression fixing means inserted in C2 enables that gap to be closed.

Compression slot C1 suitably has a longitudinal slot axis which is aligned orthogonally to the longitudinal axis 9 and preferably passes the intercondylar tibial eminence on a radius through eminence X. Aperture F4 has a removable plug (shown in FIG. 3) which is removed during the procedure and replaced by a fixing screw. In another embodiment, apertures F1 and F2 do not have a removable plug and a single removable plug is located in fixing aperture F4. At least one and preferably all of apertures F1, F2, F3 and F4 comprises engagement means for inter-engagement with the fixing means, for example the aperture is threaded and the fixing means is a screw.

Positioning aperture S2 is located at the lower extremity of the distal portion 7. The positioning apertures S1 and S2 are adapted to receive K-wire or forceps.

Slot C1 is aligned towards the locus 2 and the longitudinal slot axis of slot C1 is perpendicular to the tangent 21 (shown in FIG. 4) at the point of intersection with the locus 2. The aperture or slot C1 may be oval or any other shape to allow the fixing means to move axially along the slot during fixing. The slot C1 suitably has a chamfered or sloped profile with sloping edges 26. The fixing means suitably is shaped such that it engages with the chamfered or sloped profile upon fixing and is able to be displaced axially along the slot. Upon insertion, the fixing means engages with the underlying bone and also with the chamfered or sloped slot which acts as a camming surface to urge the fixing means towards the fracture, and thereby moves the underlying tibia 1 in which the fixing means is engaged relative to the plate thus effecting relative movement between the plate and the tibia 1. Insertion of the fixing means such as an AO cortical or cortical self-tapping screw accordingly brings the tibia and tibial fragment together. Preferably, aperture C2 is configured the same or similarly to C1.

Suitably, the TPLO plate comprises measurement markings 40, 41 disposed across the top and down the straight edge of the plate to facilitate precise location of the plate during the TPLO procedure. Preferably measurement markings 41 extend along the full length of the cranial edge of the plate. Measurement markings 40 suitably extend along the full length of the top edge of the plate. Markings 40, 41 suitably comprise a ruler marked on the plate, for example a laser marked ruler. In a preferred embodiment the ruler is marked along the edge of the proximal portion of the plate which is generally perpendicular to the axis 9. In one embodiment, the ruler provides markings to indicate a length of 15 mm, preferably with markings at 1 mm spacings.

FIG. 3 shows a plate according to the invention as shown in FIG. 2 with the plate located on a tibia 1 and tibial fragment 3 and supported by removable plugs 22, 23 in the proximal portion 8 located respectively in apertures F1 and F2 and removable plug 24 in the distal portion 7 located in aperture F4.

Figure 4:
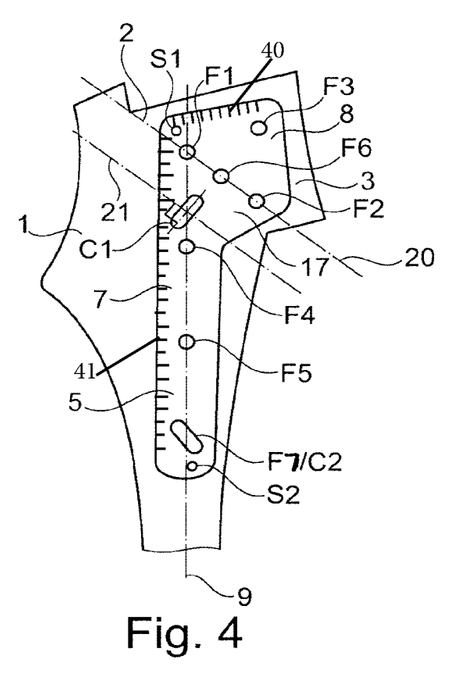
FIG. 4 shows a plan view of a plate according to the invention for use with larger canines.

FIG. 4 shows a plate according to the invention for use with larger canines than the plate in FIG. 2 and has eight fixing apertures including, as compared to the standard sized plate of FIG. 2, an additional fixing aperture F6 in the proximal portion which generally lies on the chord 20 intermediately of apertures F1 and F2. An additional fixing aperture F7 is shown in distal portion 7 which is located between aperture C2/F5 and aperture F4. The additional fixing apertures may comprise interengagement means for example a screw thread on the inner wall of the aperture. The removable plugs are located in apertures F1, F2 and F4 in the larger plate of FIG. 4 or, in an alternative embodiment, in aperture F4 only. The additional apertures F6 and F7 are provided to give additional fixing points within the plate due to the larger dimensions of the plate as compared to the plate of FIG. 2.

During a TPLO method according to the invention, after cutting the tibia 1 to provide tibial fragment 3 and rotating the fragment to the desired position, the plate is secured to the tibia 1 and tibial fragment 3 using fixing means in a particular order as follows:
 i) approximate placement of the plate using K-wires or the like in apertures S1 and S2 or vice-versa;
 ii) insertion of a screw in aperture F3;
 iii) removal of the plug from aperture F2 and insertion of a screw;
 iv) removal of the plug from aperture F1 and insertion of a screw;
 v) insertion of a compression screw in the compression slot C1, which engages with the chamfered or sloped side of the slot C1 in a camming manner and causes displacement of the tibia towards the tibial fragment along an axis of compression which is coincident with the axis of the slot C1 and passes through the intercondylar tibial eminence;

vi) drilling of a hole in the bone at C2/F5, removal of fixing means, for example K-wire from aperture S2 and insertion of a compression screw C2/F5;
vii) removal of the third plug from aperture F4 and insertion of a screw in aperture F4;
viii) optionally, if apertures F6 and F7 are present, insertion of fixing screw in F6 and F7;
ix) insertion of fixing screws in F1 and F2; and removal of K-wire from aperture S1.

In this manner, the fracture surfaces of the tibia and tibial fragment are brought together to facilitate healing whilst the plate is held proud of the bone by the plugs until they are removed.

Another method comprises the following steps:
i) approximate placement of the plate using K-wires or the like in apertures S1 and S2 or vice-versa;
ii) insertion of a locking screw in aperture F3;
iii) insertion of a compression screw in the compression hole, slot C1, which engages with the chamfered or sloped side of the slot C1 in a camming manner and causes displacement of the tibia towards the tibial fragment along an axis of compression which is coincident with the axis of the slot C1 and passes through the intercondylar tibial eminence;
iv) drilling of a hole in the bone at C2/F5, removal of fixing means, for example K-wire from aperture S2 and insertion of a compression screw C2/F5;
v) removal of the plugs from apertures F1 and F2
vi) insertion of a screw in F1 or F2 (FIG. 3) and optionally F6 (FIG. 4);
vii)
viii) removal of the third plug from aperture F4 and insertion of a screw in aperture F4 and any remaining apertures F7 and F6, if present; and
ix) removal of K-wire from S1.

Where an aperture F6 is present, the screw for F6 may be inserted before removal of the plugs from F1 and F2.

Suitably the locking screws have threaded heads for engagement with complementary threads in the apertures.

Aperture F5 is preferably a second compression aperture.

For the plate shown in FIG. 4, the same order of insertion of screws and removal of plugs is employed as with the procedure for the plate shown in FIG. 2 although, if preferred, a screw may be inserted in aperture F6 after insertion of the screw in aperture F3.

Figure 5A:
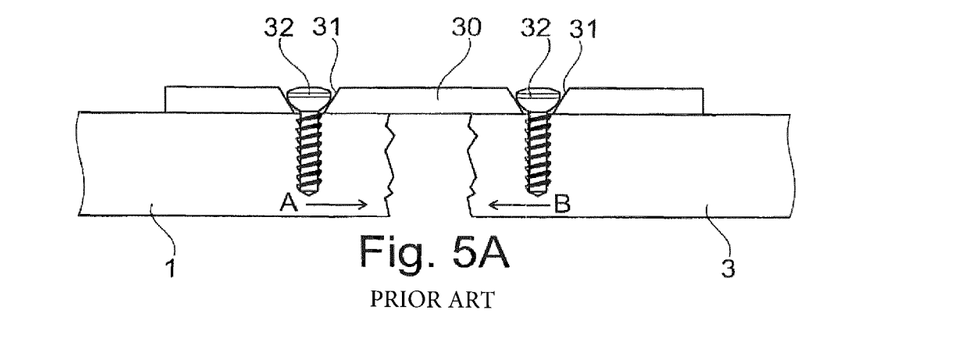
FIGS. 5A and 5B show a side view of a known plate affixed to a tibia and tibial fragment prior to final fixing (FIG. 5A) and with the fising means fully inserted in the final fixed position (FIG. 5B).

FIG. 5A shows a known plate of the prior art 30 located on a tibia 1 and a tibia fragment 3 having apertures with chamfered sides 31 in which screws 32 are located and engaged with the underlying bone and which screws 31 have surface to engage with the plate 30 such that upon inserting the screws further, the tibia 1 and tibial fragment 3 are drawn together in the directions shown by arrows A and B.

Figure 5B:
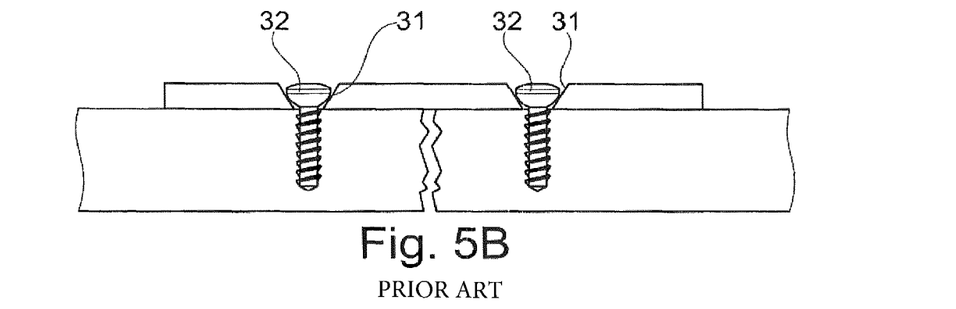

FIG. 5B shows the plate 30 with the screws 32 fully inserted such that the underside of the screw heads has engaged with the chamfered sides 31 of the apertures in plate 30 and drawn the tibia 1 and tibial fragment 3 together. Whilst the bone fragments are closer which may promote healing, the underside of plate 30 is compressed onto the bone surface which may disadvantageously cause damage or restrict blood supply.

FIG. 6 shows known screws for use in the invention and plates with a screw 32 with a chamfered head engaging the side of the aperture and causing compression of the plate against the underlying bone. Screw 33 is a self-locking screw and has a thread on the head 34 of the screw for engagement with a complementary thread 35 on the side of the aperture 36. This type of aperture/screw allows the plate to remain in its originally placed position without pulling the plate to the bone. Whilst this fixing mechanism avoids the drawbacks associated with compressing the bone surface, this does not readily enable the bone and bone fragment to be drawn together upon insertion of the screw.

FIG. 7 shows the plate of FIG. 3 with threaded apertures F1, F2 and F4 and with threaded plugs 22, 23, 24 engaged in apertures F1, F2 and F4 with the plugs and apertures having inter-engaging threads 30, 31 and 32. The degree to which the plugs are screwed into the aperture may be carefully controlled such that the depth to which the plugs protrude and abut the bone fragments 2, 3 may be determined by the surgeon according to the anatomy of the subject. Upon removal of the plugs, the surgeon simply unscrews the plug from the aperture and removes it, subsequently replacing the plug with a screw, for example a self-locking screw having a threaded head for engagement with the thread of the aperture and hence the plate.

The invention claimed is:

1. A plate for securing two bone segments in a tibial plateau levelling osteotomy procedure comprising a body having a longitudinal axis, a bone-facing surface and an outer surface, opposed to the bone-facing surface, the body comprising an elongate distal portion and a proximal portion and a plurality of apertures, the plurality of apertures comprising a first plurality of fixing apertures adapted to receive a fixing means in the elongate distal portion and a second plurality of apertures adapted to receive the fixing means in the proximal portion, wherein at least one of said apertures is adapted to receive at least one removable plug which extends proud of the bone-facing surface, wherein two of said apertures are slots, orthogonal to each other and disposed in the elongate distal portion and at least one of said slots adapted to receive the fixing means comprising a camming surface and is configured to enable transmission of a force applied to the fixing means in a direction parallel to a plane of the plate surrounding the aperture upon insertion of the fixing means, wherein the proximal portion comprises a lobe extending laterally of the longitudinal axis of the body and at least one of the slots is aligned in a direction facing the lobe of the proximal portion and aligned on a radius through an intercondylar tibial eminence.

2. A plate according to claim 1 wherein two or more of the said apertures have the at least one removable plug disposed in the aperture that extends proud of the bone-facing surface.

3. A plate according to claim 1 wherein the bone-facing surface of the body is contoured such that, in use, the body snugly overlies a tibia and tibial fragment in an alignment in which a longitudinal axis of the plate is parallel or coincident with a longitudinal axis of the tibia.

4. A plate according to claim 1 having from five to ten apertures.

5. A plate according to claim 1 wherein three of the said apertures have the at least one removable plug disposed in the aperture that extends proud of the bone-facing surface.

6. A plate according to claim 1 wherein at least one of the apertures for receiving the at least one removable plug comprises an inter-engagement means.

7. A plate according to claim 6 wherein the at least one removable plug has a screw thread adapted to inter-engage with the inter-engagement means of the aperture.

8. A plate according to claim 7 wherein two apertures in the proximal portion have the at least one removable plug located therein and one aperture in the elongate distal portion has a plug located therein.

9. A plate according to claim 1 which comprises at least two apertures for receiving a locating means for positioning the plate on the bone.

10. A plate according to claim 1 wherein the first plurality of apertures is disposed in a generally longitudinal arrangement, parallel or coincident with the longitudinal axis of the body.

11. A plate according to claim 1 wherein the first plurality of apertures comprises at least one slot, one plate positioning aperture and at least two other apertures.

12. A plate according to claim 1 wherein the bone segments have complementary curvilinear surfaces and an axis of the slot intersects a locus of the curvilinear surfaces and, when the plate is positioned in use, the axis of the slot is generally perpendicular to a tangent on the curvilinear surfaces at an intersection between the axis of the slot and the curvilinear surfaces.

13. A plate according to claim 1 wherein the second plurality of apertures is disposed towards a periphery of the proximal portion.

14. A plate according to claim 1 dimensioned for use with a small canine, medium canine or large canine.

15. A plate for securing two bone segments in a tibial plateau levelling osteotomy procedure comprising a body having a longitudinal axis, wherein the body comprises an elongate distal portion and a proximal portion and is shaped such that a first edge of the elongate distal portion and a first edge of the proximal portion together form a linear edge which extends along a length of the body and is generally parallel to the longitudinal axis wherein the body comprises a first plurality of fixing apertures adapted to receive a fixing means in the elongate distal portion and a second plurality of apertures in the proximal portion, wherein two of the first plurality of fixing apertures are slots, orthogonal to each other and at least one of the said slots adapted to receive the fixing means comprising a camming surface and is configured to enable transmission of a force applied to the fixing means in a direction parallel to a plane of the plate surrounding the aperture upon insertion of the fixing means, the proximal portion comprising a lobe extending laterally of the longitudinal axis of the body and at least one of the slots is aligned in a direction facing the lobe of the proximal portion and aligned on a radius through an intercondylar tibial eminence.

16. An orthopaedic apparatus comprising a plate for securing two bone segments in a tibial plateau levelling osteotomy procedure, the plate comprising a body having a longitudinal axis, a bone-facing surface and an outer surface, opposed to the bone-facing surface, the body comprising an elongate distal portion and a proximal portion and a plurality of apertures, wherein at least one of said apertures is adapted to receive a removable plug which extends proud of the bone-facing surface, wherein two of said apertures are slots, orthogonal to each other and disposed in the elongate distal portion and at least one of said slots adapted to receive a fixing means comprising a camming surface and is configured to enable transmission of a force applied to the fixing means in a direction parallel to a plane of the plate surrounding the aperture upon insertion of the fixing means, the proximal portion comprising a lobe extending laterally of the longitudinal axis of the body and at least one of the slots is aligned in a direction facing the lobe of the proximal portion and aligned on a radius through an intercondylar tibial eminence, the plate being in combination with the fixing means.

17. A method of carrying out a tibial plateau levelling osteotomy procedure after positioning a tibial fragment adjacent to a tibia from which the fragment has been cut comprising positioning a plate, the plate comprising a body having a longitudinal axis, a bone-facing surface and an outer surface, opposed to the bone-facing surface, the body comprising an elongate distal portion and a proximal portion and a plurality of apertures wherein at least two of the apertures are adapted to receive a fixing means and wherein at least one of the said apertures has at least one removable plug disposed in the aperture that extends proud of the bone-facing surface, wherein two of the said apertures are slots, orthogonal to each other and disposed in the distal portion and at least one of the said slots adapted to receive the fixing means comprising a camming surface and is configured to enable the transmission of a force applied to the fixing means in a direction parallel to the plane of the plate surrounding the aperture upon insertion of the fixing means, on the tibia and tibial fragment with the at least one removable plug engaging a surface of the bone; and securing the plate to the tibia and tibial fragment using the fixing means by approximate placement of the plate using a locating means, insertion of the fixing means, removal of the at least one removable plug and insertion of a screw in an aperture comprising a slot to configure the tibia and fragment into an abutting relationship.

* * * * *